US006942858B1

(12) United States Patent
Ghanbari et al.

(10) Patent No.: US 6,942,858 B1
(45) Date of Patent: Sep. 13, 2005

(54) COMPOSITIONS CONTAINING BACTERIOPHAGES AND METHODS OF USING BACTERIOPHAGES TO TREAT INFECTIONS

(75) Inventors: Hossein A. Ghanbari, Beaconsfield (CA); Paul Averback, Beaconsfield (CA)

(73) Assignee: Nymox Corporation, St. Laurent (CA)

( * ) Notice: Subject to any disclaimer, the term of this patent is extended or adjusted under 35 U.S.C. 154(b) by 0 days.

(21) Appl. No.: 09/583,738

(22) Filed: May 31, 2000

Related U.S. Application Data (62) Division of application No. 08/842,653, filed on Apr. 15, 1997, now Pat. No. 6,121,036.

(60) Provisional application No. 60/015,663, filed on Apr. 15, 1996.

(51) Int. Cl.$^7$ ............................................. A01N 63/00
(52) U.S. Cl. ............... 424/93.6; 424/184.1; 424/243.1; 424/199.1; 424/260.1; 424/191.1; 424/94.1; 514/53; 435/5; 435/6; 435/93.6; 435/253.1; 435/252.3
(58) Field of Search ............................... 424/93.6, 486, 424/473, 50, 235.1, 443, 200, 199.1, 202.1, 424/205.1, 211.1, 93.3, 239, 49, 243.1, 259.1, 424/260.1, 191.1, 94.1, 184.1; 195/103.5 R; 128/1.1; 435/5, 235.1, 93.6, 320.1, 252.3; 514/53

(56) References Cited

U.S. PATENT DOCUMENTS

| | | | |
|---|---|---|---|
| 2,851,006 A | * | 9/1958 | Taylor et al. |
| 3,793,151 A | * | 2/1974 | Denney ............... 195/103.5 R |
| 4,659,561 A | * | 4/1987 | Fives-Taylor et al. ........ 424/48 |
| 4,674,480 A | * | 6/1987 | Lemelson ................... 128/1.1 |
| 4,678,750 A | * | 7/1987 | Vandenbergh et al. ...... 435/200 |
| 4,828,999 A | * | 5/1989 | Jackson ....................... 435/235 |
| 4,891,210 A | * | 1/1990 | Norris .......................... 424/50 |
| 4,957,686 A | * | 9/1990 | Norris .......................... 424/50 |
| 5,213,808 A | * | 5/1993 | Bar-Shalom et al. ........ 424/473 |
| 5,660,812 A | * | 8/1997 | Merril et al. ................. 424/9.2 |
| 5,688,501 A | * | 11/1997 | Merril et al. ................ 424/93.6 |
| 5,714,166 A | * | 2/1998 | Tomalia et al. .............. 424/486 |
| 5,741,697 A | * | 4/1998 | Bavoil et al. ............. 435/235.1 |
| 5,766,892 A | * | 6/1998 | Merril et al. ............... 424/93.6 |
| 5,811,093 A | * | 9/1998 | Merril et al. ............... 424/93.6 |
| 6,056,954 A | * | 5/2000 | Fischetti et al. ............ 424/94.1 |
| 6,121,036 A | * | 9/2000 | Ghanbari et al. ........ 435/235.1 |
| 6,248,324 B1 | * | 6/2001 | Fischetti et al. ............ 424/94.1 |
| 6,254,866 B1 | * | 7/2001 | Fischetti et al. ............ 424/94.1 |
| 6,264,945 B1 | * | 7/2001 | Fischetti et al. ............ 424/94.1 |
| 6,271,359 B1 | * | 8/2001 | Norris et al. ............... 536/23.1 |
| 6,277,399 B1 | * | 8/2001 | Fishcetti et al. ............. 424/443 |
| 6,322,783 B1 | * | 11/2001 | Takahashi .................. 424/93.6 |
| 6,461,608 B1 | * | 10/2002 | Averback et al. .......... 424/93.6 |
| 6,482,632 B1 | * | 11/2002 | Agrawal et al. ......... 435/235.1 |
| 6,485,902 B2 | * | 11/2002 | Waddell et al. ................. 435/5 |
| 6,635,238 B2 | * | 10/2003 | Delisle ......................... 424/49 |
| 6,656,463 B2 | * | 12/2003 | Harris et al. ............... 424/93.6 |

FOREIGN PATENT DOCUMENTS

| | | |
|---|---|---|
| EP | 0 403 292 | 12/1990 |
| EP | 0403292 | * 12/1990 |
| EP | 403292 | * 12/1990 |
| EP | 0 414 304 | 2/1991 |
| EP | 0414304 | * 2/1991 |
| EP | 414304 | * 2/1991 |
| GB | 829266 | 3/1960 |
| GB | 2253859 | * 9/1992 |
| RU | 2036232 | * 5/1995 |
| RU | 153330 | * 10/1995 |
| SU | 172960 | * 7/1963 |
| SU | 827064 | * 5/1981 |
| SU | 1790380 | * 1/1993 |
| SU | 1128599 | * 5/1995 |
| SU | 1526225 | * 5/1995 |
| SU | 1412302 | * 6/1995 |
| WO | 90/03122 | * 4/1990 |
| WO | 95/27043 | 10/1995 |
| WO | 9527043 | * 10/1995 |

OTHER PUBLICATIONS

Soothil, JS (1992) Journal of Medical Microbiology, vol. 37, pp. 258-261, Treatment of experimental infection of mice with bacteriophages.*
Sekaninova, G et al, Central European Journal of public health, May 1995, vol. 3(2), pp. 80-83 (abstract only).*
Pan, R et al, ACTA Microbiol Sin. vol. 24(2), pp. 142-148, 1984, Biological characteristics of the bacteriphages of Citrobacter freundii, (abstract only).*
He, X et al, Journal of Clinical Microbiology, vol. 30(3), pp. 590-594, 1992 Bacteriophage lytic patterns for the idnetification of salmonellae, shigellae, *Escherichia coli*, Citrobacter freundii, and Enteroacter cloacae (abstract only).*
UK: Studies found enteric bacterial infections may be better treated with bacteriophages than with antibiotic therapy. Scrip, Nov. 23, 1983, p. 16 (abstract only).*
Slopek, S et al, Archivum immunologiae et therapiae experimentalis, vol. 35(5), pp. 569-583, 1987, Results of bacteriophage treatment of suppurative bacterial infection in the years 1981-1986 (abstract only).*

(Continued)

*Primary Examiner*—Lynette R. F. Smith
*Assistant Examiner*—Ginny Allen Portner
(74) *Attorney, Agent, or Firm*—Foley & Lardner LLP (57) ABSTRACT

Purified, host-specific, non-toxic, wide host range and virulent bacteriophage preparations that are effective in killing bacterial organisms in vivo are disclosed. Also disclosed are compositions containing these bacteriophages, methods of making the bacteriophage preparations and methods of treating bacterial infections using the compositions. Methods of treating bacterial infections using the compositions containing the bacteriophages in combination with conventional antibiotics also are disclosed.

12 Claims, 7 Drawing Sheets

OTHER PUBLICATIONS

Bogovazova, GG et al, Zhurnal mikrobiologii, epidemiologii, i immunobiologii, Apr. 1991, vol. 4, pp. 5-8, The efficacy of Klebsiella pneumoniae bacteriophage in the terapy of experimental infection (abstract only).*

Sakandelidze, VM, Vrachebnoe delo, (USSR), Mar. 1991, vol. 3, pp. 60-63, The combined use of specific phages and antibiotics in infectious allergoses. (abstract only).* de Vries, GE et al, Proceedings of the National Academy of Sciences of the United States of America, Oct. 1984, vol. 81(19), pp. 6080-6084 (abstract only).*

Bogovazova, GG etal, Zhurnal mikrobiologii, epidemiologii, i immunobiologii, Mar. 1992, vol. 3, pp. 30-33, English abstract and russian pages.*

Fel'dman, lu M et al, Zhurnal mikrobiologii, epidemiologii, i immunobiologii, Oct. 1975, vol. 10, pp. 59060, English abstract and Russian pages.*

Reynaud, A etal, Veterinary microbiology, Feb. 1992, vol. 30(2-3), pp. 203-212.*

Williams, Smith H et al, Journal of General Microbiology, vol. 129(8), pp. 2659-2675, 1983 (abstract only).*

American Type Cuture Collection Deposited Strains: ☐☐ATCC 21597-B1; ATCC 8014-B2; ATCC 8014 B1; ATCC 27139-B1.*

Smith et al., "The Control of Experimental *Escherichia coli* Diarrhoea in Calves by Means of Bacteriophages" *Journal of General Microbiology* 133:1111-1126 (1987).

Smith et al. "Successful Treatment of Experimental *Escherichia coli* Infections in Mice Using Phage; its General Superiority over Antibiotics" *Journal of General Microbiology* 128:307-318 (1982).

XP 002036010 *Derwent Publication Ltd.* Abstract (1991).

Barrow et al., 1997 Trends in Microbiology 5 (7) p 268-271.

Dubos et al., 1943 Journal of Experimental Medicine vol. 78 161-168.

Levin et al., 1996, The American Naturalist 147 (6) p. 881-898.

Rodicio et al., 1982, Journal of Bacteriology 151 (3) pp 1078-1085.

* cited by examiner

COMPOSITIONS CONTAINING BACTERIOPHAGES AND METHODS OF USING BACTERIOPHAGES TO TREAT INFECTIONS

This application is a divisional of U.S. application Ser. No. 08/842,653, filed Apr. 15, 1997, now U.S. Pat. No. 6,121,036 which is based on provisional Application Ser. No. 60/015,663, filed Apr. 15, 1996.

BACKGROUND OF THE INVENTION

1. Field of the Invention

The present invention relates to the use of bacteriophages to treat infectious diseases whereby the host-specific, wide host-range bacteriophages are present, in purified form, in non-toxic sufficiently virulent compositions that can be administered to patients or mammals in need thereof. The bacteriophages are useful in treating infections due to bacterial microorganisms by killing a sufficient quantity of the bacterial microorganisms or by rendering the bacterial microorganisms more susceptible to other chemotherapeutic antibiotics.

2. Description of Related Art

Bacteriophages (phages) are a heterogeneous group of viruses that infect bacteria that were first discovered in the early part of the 20th century. d'Herelle, F., *The bacteriophage. Its role in immunity*, translated by Smith, G. H., Williams & Wilkins Co., Baltimore (1922). Bacteriophages presently are widely used in scientific research, such as in molecular biology (e.g. as genetic vectors) and in medical diagnostics (e.g. phage typing of bacteria). Insofar as phages naturally infect and kill bacteria, it traditionally was suggested that they could be utilized in medical therapeutics, because bacteria are a major cause of disease.

Indeed, potential therapeutic uses of phage in experimental systems have been reported extensively in the literature (d'Herelle, F., *The bacteriophage and its clinical applications*, Charles C. Thomas, Baltimore (1930)). None of these potential experimental therapeutic uses has resulted in the formulation of an efficacious bacteriophage preparation, i.e., one that is sufficiently virulent, non-toxic, host-specific, and with wide enough host range to be of practical use. The notion of phage therapeutics has not resulted in practical usage because: (i) efficacy has been marginal or non-existent; (ii) toxic side effects of phage therapy have been unacceptable; (iii) better alternatives such as conventional chemical antibiotics have existed; (iv) conventional bacteriophage preparations are contaminated with debris from bacterial lysis which typically contain toxins; (v) an antibody response to the bacteria can be initiated upon introduction of the phage; and (v) phage preparations do not arrive at the target site because they are removed too fast from the body once injected or ingested. Thus, with respect to phage therapeutics in the use of ameliorating or treating specific animal infections, there is no currently known practical workable concept or method. Ostensibly, therefore, there is practically no known specifically useful phage therapeutic or composition of matter containing a phage therapeutic. In addition to the above general limitations, there also have been little or no reported advantages for the use of phage therapeutics such as, for example, (i) useful innovations for administration of phage therapy, (ii) adjunctive therapeutic use of phage therapy with other antibiotherapeutics, or (iii) for use in the context of microorganism resistance to conventional therapies.

Despite the recognized value and importance of new antimicrobial therapies, the potential of phage therapy has not been accomplished in any practical sense that is used in modern therapeutics, nor have methods, compositions, or other uses been defined for nontoxic and efficacious therapies of this type with practical and effective delivery. Phage preparations known in the art and available today are not known to be effective in treating mammalian bacterial infections (AMERICAN TYPE CULTURE COLLECTION CATALOGUE OF BACTERIA AND BACTERIOPHAGES, (ATCC) 18th Edition, pages 402–411 (1992). It is believed that conventional, or wild-type phage preparations are: (i) incapable of surviving for sufficient periods of time in vivo; (ii) impure in that they contain various strains of bacteriophage including mutated phage and the like which are not virulent to the respective bacterial microorganism, as well as a host of bacterial impurities; (iii) toxic; and (iv) not host-specific in that they do not tend to migrate primarily to the bacterial infections.

Recent approaches have attempted to make use of phage therapeutics by utilizing bacteriophages that are selected using a specific serial passage method to produce longer circulating bacteriophages. Specific bacteriophages have been developed to *Escherichia coli* and *Salmonella typhimurium* by first isolating bacteriophages and mutants thereof that are specific to these bacterial microorganisms, and then purifying these bacteriophages and selecting the strains that are capable of avoiding entrapment in the reticuloendothelial system of the animal by consecutive cycles of injecting the phage into the animal, isolating the phage in the blood of the animal and regrowth of the phage in the bacteria. The use of this serial passage method in ascertaining efficacious bacteriophage, however, is extremely costly and time consuming to develop and it is of known usefulness in the majority of infections. Furthermore, a longer circulating bacteriophage is not precluded from being less virulent and therefore ineffective as a potential or theoretical treatment. This method of developing bacteriophage preparations therefore is undesirable, and the selection criteria utilized likely will not yield a virulent, non-toxic host-specific bacteriophage preparation.

One of the primary reasons why bacteriophages have not been utilized to treat bacterial infections and bacterial microorganisms is due to the widespread use of antibiotics. Numerous strains of bacteria and microorganisms have evolved, however, which are resistant to conventional antibiotics. There exists a need, therefore, to develop methods of treating bacterial infections that are resistant to conventional antibiotics or to develop a method that can complement the antibiotherapy.

In addition, there exists a need to develop new and useful phage therapeutics which can be used to treat infectious disorders caused by bacterial microorganisms. There also exists a need to develop compositions including phage therapeutics in pharmaceutically acceptable vehicles that can be administered to subjects infected with bacterial microorganisms. There is an additional need to develop a method that is capable of delineating useful phage therapeutics that is efficient and economically feasible. There also exists a need to develop new and useful phage therapeutics that are useful in combination with antibiotics to treat infectious disorders caused by bacterial microorganism infection. Finally, there exists a need to develop a bacteriophage preparation that is host-specific, virulent and non-toxic thereby rendering it useful in treating bacterial infections.

Examination of past failures with phage therapeutic attempts and modern approaches to these failures, have now revealed that phages used for antibacterial therapies in certain specific situations are highly important which make this new type of treatment very attractive and useful. The bacteriophage preparations, however, must be selected so that virulent, non-toxic, host-specific preparations are formulated. Thus, there is a need to develop host-specific, non-toxic and virulent bacteriophage preparations that can be used to effectively treat bacterial infections in a mammal.

SUMMARY OF THE INVENTION

It is therefore an object of the present invention to develop new and useful phage therapeutics which can be used to treat infectious disorders caused by bacterial microorganism infections. Another object of the invention is to provide a bacteriophage preparation that is virulent, non-toxic and host-specific. It is an additional object of the present invention to provide a method of screening effective phage therapeutics that is efficient and economically feasible. It is a further object of the present invention to provide new and useful phage therapeutics that can be used in combination with antibiotics to treat infectious disorders. It is yet another object of the present invention to provide a method of treatment using phage therapeutics in novel vehicle preparations for treating animal infections caused by microorganisms.

In accordance with these objectives, there is provided a composition comprising a microorganism host specific non-toxic purified phage preparation specific to a microorganism including, inter alia, *staphylococci, hemophilii, helicobacter, mycobacterium, mycoplasmi, streptococci, neisserii, klebsiella, enterobacter, proteus, bacteriodes, pseudomonas, borrelii, citrobacter, escherichia, salmonella, propionibacterium, treponema, shigella*, enterococci and *leptospirex*. Preferably the micoorganism includes, inter alia, *Staphylococcus aureus, Staphylococcus epidermidis, Helicobacter pylori, Streptococcus pneumoniae, Streptococcus mutans, Streptococcus oralis, Streptococcus parasanguis, Streptococcus pyogenes, Streptococcus viridans*, Group A *streptococcus* and anaerobic *streptococcus, Hemophilus influenzae, Shigella dysenteriae, Mycobacterium tuberculosis, Mycobacterium leprae, Mycobacterium asiaticum, Mycobacterium intracellulare, Mycoplasma pneumoniae, Mycoplasma hominis, Neisseria meningitidis, Neisseria gonorrhea, Klebsiella pneumoniae, Pseudomonas aeruginosa, Propionibacterium acnes, Treponema pallidum, Treponema pertanue, Treponema carateum, Escherichia coli, Salmonella typhimurium, Borrelia burgdorferi, Leptospirex*, such as *Leptospirex hemoragia Citrobacter fruendii*, and the like. There also are provided compositions comprising the aforementioned phage preparations either in aqueous injectable form or in the form of liposomes, a topical preparation, a transdermal patch or other capsule which may obviate administration by injection.

In accordance with an additional object of the present invention, there is provided a method of screening efficacious phage therapeutics by selecting phages that are more virulent and more adaptable in vivo thereby rendering them more capable of survival in vivo and more capable of infecting and killing bacteria. In accordance with this object of the present invention, bacteriophages can be selected which: (i) have a higher frequency per unit volume of foci of bacterial killing (plaque forming units per volume); (ii) have a higher frequency per unit volume of foci of bacterial killing with a smaller volume of phage preparations; and (iii) are capable of killing a wider range of host bacteria from a wider range of different isolated cultures of a given bacteria, i.e., a wide host range. Other techniques useful for selecting bacteriophage include selecting those that: (i) are resistant to exposure to high temperatures or drying; (ii) are resistant to exposure to lytic agents or mutator hosts; (iii) survive for a period of time greater than 24 hours under normal or abnormal conditions; (iv) are resistant to heat shock; and/or (v) are resistant to ionic variation including drying, overhydration or extremes of individual ionic concentrations.

In accordance with an additional object of the invention, there is provided a method of making a host-specific, non-toxic and virulent bacteriophage preparation whereby the preparation includes a bacteriophage that is effective in killing bacterial organisms in vivo. The method includes obtaining a sample containing a bacteriophage to at least one bacterial organism selected from staphylococci, hemophilii, *helicobacter, mycobacterium*, mycoplasmi, streptococci, neisserii, *klebsiella, enterobacter, proteus, bacteriodes, pseudomonas, borrehii, citrobacter, escherichia, salmonella, propionibacterium, treponema, shigella*, enterococci and *leptospirex*. The sample then is dispersed in phosphate buffered saline, filtered through a filter that will retain the bacterial organism and allow the bacteriophage to pass and the resulting bacteriophage is purified. Bacteriophage then are grown in a medium containing at least one of the bacterial organisms, and bacteriophage preparations achieving titers higher than about $10^8$ to $10^9$ bacteriophages per plaque after about eight hours are selected and isolated to provide an isolated bacteriophage. The isolated bacteriophage then is purified and the purified bacteriophage is again grown in a medium containing at least one of the bacterial organisms. This procedure of growing the bacteriophage in a medium containing at least one of the bacterial organisms, selecting, isolating and purifying the bacteriophage then is repeated anywhere from about 5 to about 25 times, and a bacteriophage that is virulent and capable of killing a wide host range of bacterial organisms is selected, isolated and purified to prepare a host-specific, non-toxic and virulent bacteriophage preparation.

In accordance with an additional object of the present invention, there is provided a method of making a host-specific, non-toxic virulent bacteriophage preparation whereby the preparation includes a bacteriophage that is effective in killing bacterial organisms in vivo. The method includes obtaining a sample containing a bacteriophage to at least one bacterial organism listed above, dispersing the sample in saline, filtering through a filter that will retain the bacterial organism and allow the bacteriophage to pass and the resulting bacteriophage is purified. The purified bacteriophage then are grown in a medium containing at least one of the bacterial organisms, and bacteriophage preparations achieving titers higher than about $10^8$ to $10^9$ bacteriophages per plaque after about eight hours are selected and isolated to provide an isolated bacteriophage. This procedure can be repeated once, twice or up to 30 times, if desired to produce a purified and isolated bacteriophage. The purified and isolated bacteriophage then is subjected to at least one mutating condition selected from mutator host, irradiation, temperature and pH extremes, ionic variation, drying or overhydration, extreme ionic concentration and heat shock, whereby at least one bacteriophage survives the mutating condition. The bacteriophage that survives then is isolated and purified to prepare a host-specific, non-toxic and virulent bacteriophage preparation.

In accordance with another object of the present invention, there is provided a method of treating a mammal infected with a microorganism selected from any of the microorganisms listed above whereby the method includes administering to the mammal a therapeutically effective amount of the aforementioned composition. In accordance with yet another object of the present invention, there is provided a method of treating a mammal infected with the aforementioned microorganisms comprising administering to the mammal a therapeutically effective amount of the aforementioned composition in combination with an antibiotic. In accordance with these methods, the aforementioned compositions can be administered by routes including but not limited to intravascular injection, oral, intranasal, topical, sub-trans- and intracutaneously, and by other routes.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Throughout this description, the expression "wide host range" denotes a bacteriophage that is capable of killing bacteria from a variety of different hosts. Preferably, the bacteriophage of the present invention are capable of killing bacteria from at least about 50% of the host samples. Throughout this description, the term "virulent" denotes a bacteriophage that is capable of effectively killing bacteria from a wide host range. Preferably, the bacteriophage that are selected are effective in killing about 100% more bacteria from various sources, or hosts, when compared to the bacteriophage that are not selected. More preferably, the bacteriophage are selected that kill about 200% more bacteria, and most preferably, bacteriophage are selected that kill about 300% more bacteria. For example, by means of illustration only, assume that two bacteriophage preparations are selected and each are tested against bacteria samples from 100 different hosts. If the first one is effective in killing bacteria from 15 hosts, and the second is effective in killing bacteria from 60 hosts, then the second bacteriophage preparation would be virulent and would have a wider host range, and the second bacteriophage preparation would killing 300% more bacteria than the first.

"Virulent bacteriophage preparations" also denotes bacteriophage preparations that are capable of killing bacteria at a lower concentration than non-selected non-virulent bacteriophage. For example, and for purposes of illustration only, assume that two bacteriophage preparations are selected and the first one is effective in killing bacteria at $10^6$ dilution. If the second phage preparation is effective in killing bacteria at $10^8$ dilution, then the second phage preparation can be said to be virulent, when compared to the first. The expression "non-selected bacteriophage" denotes bacteriophage preparations that are prepared together with the virulent, host-specific, purified, wide host range and non-toxic bacteriophage of the present invention, but are not selected because they are less virulent, and/or are less host-specific, and/or have a much narrower host-range, and/or are toxic and/or are not purified. Hence, the bacteriophage preparations prepared and selected in accordance with the present invention are even more superior, when compared to the non-selected bacteriophage, in terms of virulence, host-specificity, host range, toxicity and purity than commercially available, or wild-type bacteriophage preparations that are available from the Center for Disease Control (CDC) or the ATCC.

In accordance with the present invention, it has been determined that host-specific, virulent and non-toxic bacteriophage preparations can be used to treat specific bacterial infections. Particularly effective in this regard are host-specific, non-toxic and purified phage preparations which act by killing the microorganism, and which act on specific infections by obliterating sufficient numbers of the microorganisms present in the infectious focus. Throughout this description, the expression "purified" denotes a phage preparation that contains substantially no toxins, (no endotoxins) preferably less than 1.0% by weight of toxins (endotoxins) and more preferably less than about 0.05% by weight of toxins (endotoxins). Traditional bacteriophage preparations that were known to be inefficacious in vivo were not host-specific, typically were not purified, usually were toxic and typically were not virulent in vivo. The bacteriophage preparations according to the present invention, however, have alleviated these problems in that the inventive phage preparations are selected, using the guidelines provided herein, to be highly host specific, non-toxic and purified to the extent that renders the inventive phage preparations effective in killing and/or obliterating and/or reducing sufficient numbers of host bacteria in vivo.

Host-specific, non-toxic, wide host range, virulent and purified phage preparations also can be used that reduce but do not entirely obliterate the population of microorganisms, thereby rendering the infectious focus more susceptible to other chemotherapeutic antibiotics and thus reducing in combination therapy duration, side effects, and risks of the latter. Thus, the phage preparations in this embodiment of the invention preferably can be used in combination with known antibiotics such as aminoglycosides, cephalosporins, macrolides, erythromycin, monobactams, penicillins, quinolones, sulfonamides, tetracycline, and various anti-infective agents. Those skilled in the art can refer to the Physician's Desk Reference, 50th Ed (Medical Economics (1996)), or similar reference manuals for a more complete listing of known antibiotics which could be used in combination with the inventive phage preparations. For example, a phage preparation effective against various strains of *staphylococcus* could be used in combination with a cephalosporin such as Keflex® or Keftab® (both from Cephalexin). Those skilled in the art, using the guidelines provided herein, are capable of designing an effective treatment regimen by either using the phage preparation alone or using a phage preparation in combination with antibiotics.

The host-specific, non-toxic and purified phage preparations of the invention can be prepared by growing in the presence of a microorganism including, inter alia, staphylococci, hemophilii, *helicobacter, mycobacterium*, mycoplasmi, streptococci, neisserii, *klebsiella, enterobacter, proteus, bacteriodes, pseudomonas, borrehii, citrobacter, escherichia, salmonella, propionibacterium, treponema, shigella*, enterococci and *leptospirex*. Preferably the micoorganism includes, inter alia, *Staphylococcus aureus, Staphylococcus epidermidis, Helicobacter pylori, Streptococcus pneumoniae, Streptococcus mutans, Streptococcus oralis, Streptococcus parasanguis, Streptococcus pyogenes, Streptococcus viridans*, Group A *streptococcus* and anaerobic *streptococcus, Hemophilus influenzae, Shigella dysenteriae, Mycobacterium tuberculosis, Mycobacterium leprae, Mycobacterium asiaticum, Mycobacterium intracellulare, Mycoplasma pneumoniae, Mycoplasma hominis, Neisseria meningitidis, Neisseria gonorrhea, Klebsiella pneumoniae, Pseudomonas aeruginosa, Propionibacterium acnes, Treponema pallidum, Treponema pertanue, Treponema carateum, Escherichia coli, Salmonella typhimurium, Borrelia burgdorferi, Leptospirex*, such as *Leptospirex hemoragia Citrobacter fruendii*. More preferably, the microorganism is selected from any one of staphylococci, streptococci, *citrobacter, escherichia* and *klebsiella*, and most preferably, the microorganism is selected from *Staphylococcus aureus, Streptococcus pyogenes, Klebsiella oxytoca, Escherichia coli* and *Citrobacter, fruendii*.

The phages employed according to the present invention can be any phages capable of infecting and killing bacteria and bacterial infections in mammals. Preferably, the phages of the invention can initially be derived from microorganisms by standard methods well known to those skilled in the art or can be obtained from various depositories. AMERICAN TYPE CULTURE COLLECTION CATALOGUE OF BACTERIA AND BACTERIOPHAGES, 18th Edition, pages. 402–411 (1992). Selection of phage for virulence and persistence then can be effected by methods such as repeated growth in bacteria followed by selection, isolation and purification of phage from plaque forming units, as well as selection based on resistance to physical methods such as temperature and/or drying, or by biochemical-toxic methods such as exposure to lytic agents or mutator hosts, or by longevity of survival under normal or abnormal conditions. After culture with or without selection for virulence, specific phage can be purified to homogeneity. This can be accomplished by filtration, plaque formation, and analytical density gradient ultracentrifugation in gradients such as sucrose, Ficoll, Percoll or cesium chloride. Those skilled in the art are capable of selecting and purifying a given phage preparation using the guidelines provided herein, coupled with known purification techniques.

To be effective in killing and/or obliterating bacterial microorganisms, or to be capable of reducing sufficient quantities of these microorganisms, the bacteriophages of the present invention are subjected to the above-mentioned selection methods to specifically select the virulent bacteriophage. Phage preparations known in the art and available today are not known to be effective in treating mammalian bacterial infections (ATCC CATALOGUE OF BACTERIA AND BACTERIOPHAGES, 18th Edition, pages 402–411 (1992). While not intending to be bound by any theories, it is believed that conventional phage preparations are: (i) incapable of surviving for sufficient periods of time in vivo; (ii) impure in that they contain various strains of bacteriophage including mutated phage and the like which are not virulent to the respective bacterial microorganism, as well as a host of bacterial impurities; (iii) toxic; and (iv) not host-specific in that they do not tend to migrate primarily to the bacterial infections. The phage preparations of the present invention do not suffer from these drawbacks, however, because the inventive phage preparations are selected for virulence and specificity, and are purified and concentrated. The inventive, phage preparations therefore are efficacious in vivo in killing, obliterating or reducing sufficient quantities of bacterial microorganisms.

Various mechanisms can be used to select bacteriophage preparations for virulence. Initially, however, bacteriophage preparations must be derived from microorganisms, which can be effected using methods known in the art. (See, AMERICAN TYPE CULTURE COLLECTION CATALOGUE OF BACTERIA AND BACTERIOPHAGES, 18th Edition, pages 402411 (1992). For example, samples can be collected from individuals who suffer from a bacterial infection. Various samples can be taken from various places on the body including the throat, blood, urine, feces, spinal fluid, nasal mucosa, skin, washings from the larynx and trachea, and the like. Sample sites can be selected depending upon the target organism. For example, a throat swab likely would be used to collect a sample of a given strain of *streptococcus*, a skin culture likely would be used to collect a sample of a given strain of *staphylococcus*, a spinal fluid or blood sample likely would be used to collect a sample of *Neissereia meningitidis*, a urine sample can be used to collect samples of *E. coli*, and the like. Those skilled in the art are capable of obtaining an appropriate sample from the respective locus, given the target organism. Alternatively, bacterial strains can be obtained from various laboratories including those available from the National Institutes for Health (NIH), the ATCC and the like.

Preferably, samples are obtained from various medical professionals, the samples are purified, and colonies of the bacteria are grown using conventional methods. When a bacterial organism is identified from any of the aforementioned sources, it preferably is grown in pure culture and frozen for storage at about −20° C., −70° C. and −80° C. These organisms can be frozen using conventional methods. A particularly preferred method for freezing bacterial samples includes preparing overnight cultures of bacterial isolates, and then adding about 400 μl of a sterile 80% glycerol to about 1 ml of overnight culture. The microtubes then can be labeled and stored at −20° C., −70° C. and −80° C.

These samples then can be used to generate the bacteriophage preparations by dispersing the sample in a solution, for example, a phosphate buffered saline solution, and then filtering the solution through a very small pore size filter to retain the target organism and permit the bacteriophage to pass through. Preferably, a filter having a pore size in the range of from about 0.01 to 1 μm can be used, more preferably, from about 0.1 to about 0.5 μm and most preferably from about 0.2 to about 0.4 μm. Bacteriophage preparations then can be generated by growing in a medium containing the target organism with periodic titering. The bacteriophage samples are taken periodically, preferably about every 2 hours and the quantity of bacteriophage titered. Those skilled in the art are capable of growing bacteriophage in the bacterial host using conventional methods such as those described in, inter alia, Silhavy et al., EXPERIMENTS WITH GENE FUSION, Cold Spring Harbor Laboratory, Cold Spring Harbor, N.Y. (1984).

When a sufficient quantity of bacteriophage is achieved, preferably about $10^5$ to about $10^{10}$, usually about $10^8$ to about $10^9$, the phage preparations can be isolated using filtration with filters such as those described above, and the samples can be purified by centrifugation, for example, using cesium chloride density centrifugation as described in Sambrook et al., MOLECULAR CLONING: A LABORATORY MANUAL, $2^{nd}$ Edition, Cold Spring Harbor, N.Y., pp. 2.73–2.81 (1989). Usually, the bacteriophage preparations achieving higher titers at earlier sampling times are selected and separated. Those skilled in the art are capable of selecting and separating the appropriate bacteriophage using the guidelines presented herein. Preferably, this method of growing the phage in a medium containing the bacteria, and then selecting, isolating and purifying phage from plaque forming units is repeated a number of times until a virulent phage preparations is obtained. Most preferably, the method is repeated from about 5 to about 25 times.

Upon separating, or while growing in the medium together with the host or target organism, the bacteriophage also can be selected for virulence by subjecting it to various stringent conditions. For example, the phage preparation can be subjected to mutating conditions using a mutator host. Alternatively, the phage preparation medium can be subjected to irradiation by light and/or heat, it can be subjected to extreme variations in pH by addition of appropriate acid or caustic, the medium can be subjected to overhydration or to drying conditions, extreme individual ionic concentration or heat shock. These various procedures are conducted on the phage medium to assure bacteriophage diversity and to increase the probability of selecting more virulent and more in vivo adaptable bacteriophages. Those bacteriophages that survive the aforementioned conditions then are separated using the methods described above, and purified. If desired, additional bacteriophage can be generated or cloned using techniques known to those skilled in the art, and the resulting preparations purified. Skilled artisans are capable of carrying out the aforementioned testing methodology to select virulent phage preparations, using the guidelines provided herein, and also are capable of separating and purifying the virulent phage preparations that survive any and/or all of the aforementioned testing protocol.

These bacteriophage preparations then optionally can be administered to a test animal, for example, a mouse, by injection and samples can be withdrawn at various sites (i.e., skin samples, throat swabs, nasal mucosa samples, rectal samples, blood samples and the like). The bacteriophage samples that are the most virulent can be determined by plating by using standard methods. The bacteriophage samples that are the most virulent then can be isolated, grown, purified and detoxified, if needed.

These purified bacteriophage preparations then can be administered to a test animal that has been infected with the respective bacterial microorganism. The virulence of the bacteriophage preparations can be determined by comparing the microbial counts of bacteriophage from infected animals versus the microbial counts for non-infected, or control, animals. The bacteriophage preparations having the highest anti-bacterial activity then can be selected, isolated and purified. The resulting bacteriophage preparation then can be detoxified using techniques known in the art.

For example, the purified bacteriophage preparation can be subjected to ultrafiltration through a membrane or hollow fiber with a molecular weight cut-off of approximately $10^4$ to about $10^7$ daltons, preferably within the range of from about $10^5$ to about $10^6$ daltons. Alternatively, the phage preparations can be subjected to ultracentrifugation using preparations such as cesium chloride (i.e., at a concentration range of from about 60 to about 95 grams per mole), percoll, ficoll, (i.e., at about 50 to about 80%) or sucrose and glycerol (i.e., at about 5% to about 40%). Ultracentrifugation can be carried out at forces within the range of from about 50,000×g to about 90,000×g, preferably from about 60,000×g to about 80,000×g, for 2 or more hours for cesium chloride, sucrose and glycerol, or for example, from about 20,000×g to about 40,000×g, preferably from about 25,000×g to about 35,000×g for 20 to 30 minutes using percoll or ficoll.

In addition, the phage preparations can be detoxified by dialysis using the largest pore membrane that retains bacteriophages, where the membrane preferably has a molecular weight cut-off of approximately $10^4$ to about $10^7$ daltons, preferably within the range of from about $10^5$ to about $10^6$ daltons. Alternatively, the phage preparations can be detoxified using size exclusion chromatography using preparatory columns with an exclusion pore of any where from about $10^4$ to about $10^7$ daltons, preferably from about $10^5$ to about $10^6$ daltons.

These purified phage preparations which have been selected for virulence then can be formulated into compositions that can be administered in large enough dosage and in adequate frequency to effect arrest or retardation of infection. The above durations and dosages can be determined on a specific basis for each specific type of phage in each specific type of infection in each specific host. Thus, those skilled in the art will recognize that the effective dosage in a mouse will differ from that of a man, and will also vary according to the specific microorganism. The quantitative determinations can be readily determined by one of ordinary skill in the art.

The compositions of the present invention can be prepared by admixing a quantity of purified phage preparation with a pharmaceutically acceptable carrier. Usually, the compositions of the present invention are advantageously administered in the form of injectable compositions. A typical composition for such purpose comprises a pharmaceutically acceptable carrier. For instance, the composition may contain about 10 mg of human serum albumin and from about 20 to 200 micrograms of the phage preparation per milliliter of phosphate buffer containing NaCl. Other pharmaceutically acceptable carriers include aqueous solutions, non-toxic excipients, including salts, preservatives, buffers and the like, as described in REMINGTBN'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Examples of non-aqueous solvents include propylene glycol, polyethylene glycol, vegetable oil and injectable organic esters such as ethyloleate. Aqueous carriers can include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the bacteriophage compositions of the invention can be adjusted according to routine skill in the art. See GOODMAN AND GILMAN'S THE PHARMACOLOGICAL BASIS FOR THERAPEUTICS (7th ed.).

Advantageously, the bacteriophage compositions of the present invention can be in the form of liposomes, lipophilic microcapsules, dendrimers or the like for oral administration to treat systemic infections. Those skilled in the art are capable of preparing the phage preparations of the present invention in the form of a lipophilic microcapsule, a dendrimer or a liposome using conventional techniques known in the art. The skilled artisan also is capable of providing a bacteriophage preparation composition that can be administered intranasally, rectally, transdermally, topically, or other known routes of administration of medicaments.

The compositions of the present invention can be used to treat mammals having bacterial infections. Specifically, the compositions of the present invention are useful in treating mammals infected with any of the bacterial microorganisms listed above. Suitable bacteriophage-containing compositions can be prepared that will be effective in killing, obliterating or reducing the quantity of any of the aforementioned bacterial microorganisms using the guidelines presented above.

The compositions of the present invention preferably are administered intravenously, intranasally, orally, etc., in an amount and for a period of time effective to treat the bacterial infection. The expression "treating bacterial infections," as it is used throughout this description, denotes either (i) killing or obliterating sufficient bacterial microorganisms to render the microorganisms ineffective in infecting the host, or (ii) reducing a sufficient quantity of bacterial microorganisms so as the render the microorganisms more susceptible to treatment using conventional antibiotics. Determining an effective amount of host-specific, non-toxic purified phage preparation to be administered in accordance with the present invention entails standard evaluations. An assessment in this regard would generate data concerning bioavailability, absorption, metabolism, serum and tissue levels and excretion, as well as microorganism levels, markers, and cultures. The appropriate dosage and duration of treatment can be ascertained by those skilled in the art using known techniques.

The present invention now will be illustrated by the following examples which are intended to further exemplify particularly preferred embodiments of the invention, and are not meant to limit the invention.

The wild-type bacteriophage samples obtained from publicly available sources such as the ATCC or CDC are not suitable for therapeutic use because they are not non-toxic, host-specific, virulent, purified or they do not have a wide host range. In contrast, bacteriophage preparations prepared in accordance with the foregoing description and following examples are suitable for therapeutic use because they are non-toxic, host-specific, virulent, purified and have a wide host range.

EXAMPLES

Example One

The following procedure can be followed to prepare purified, toxin-free phage preparations specific to any of the bacterial microorganisms listed above. Bacteriophage specific to any of these microorganisms can be grown in vitro or in vivo in a test animal such as a mouse using methods known in the art. Wood, W. B., et al., *Building a Bacterial Virus*, Scientific American, (1967). Samples of materials containing the bacteriophage then are collected and further treated to isolate and purify the bacteriophage.

The phage purification and toxin removal will be accomplished by differential centrifugation, serial filtration and size exclusion chromatography. Toxins are removed thoroughly by surfactants of high non-ionic strength as well as dissociating compounds (urea and sucrose). Commercial kits are used to monitor toxin contamination. (Limulus Amebocyte Lysate Assay, Associates of Cape Cod Inc., Woods Hole Mass.).

Example Two

The purified phage preparation suitable for oral administration to treat systemic infections is prepared by packaging the phage preparation into highly lipophilic microcapsules such as liposomes or dendrimers. Delivery also is effected by the transnasal route.

Example Three

The following procedure can be followed to determine the clinical efficacy of the host-specific, non-toxic purified phage preparation of Example 1, or the phage compositions of Example 2.

Test One

Test animals such as dogs, rats, monkeys or other species are subjected to lethal doses of bacteria such as *klebsiella* or *enterobacter* and are observed clinically and microbiologically. Equal numbers of such animals subjected to the above lethal doses also are treated with adequate dosages of the phage preparations of Example 1 delivered by intravenous, intraperitoneal, intramuscular, transcutaneous or other route by adequate vehicle such as liposome or patch or other capsule obviating injection, and are observed clinically and microbiologically.

Results: Results are assayed in clinical and microbiological terms. Cultures from treated versus non-treated animals with quantitative titers show that the host-specific non-toxic purified phage preparations of Example 1 inhibits infection significantly. Clinical examinations of treated versus untreated animals show that the host-specific non-toxic purified phage preparations of Example 1 inhibits infection significantly. In untreated animals infected with lethal dosages as above, progressive deterioration leading to death is found in all or practically all cases. Progressive deterioration often includes but is not limited to: fever, lethargy, and fluid imbalance and secondary symptoms, and may include hyperactivity, seizures, hemorrhage, and other manifestations. In sharp contrast to the un-treated animals, treated animals eliminate the bacteria and return to pre-infection clinical status. Clinical evolution in treated cases depends on the duration of pretreatment inoculation, which in turn determines severity of pretreatment infection development.

Other assays of treatment efficacy are within the scope of the present invention, such as non-microbiologic serologic and hematologic tests such as erythrocyte sedimentation rate, blood cell counts, antibody response, or radiological, scanning or other procedures well known to health care and research personnel.

Example Four

The following method can be used for preparation of virulent phage preparations for specific use in treating specific bacterial infections. Experimental animals are infected with a specific microorganism at a standard dosage and then cultures with higher titer of phage are selected for phage usage. Alternatively, cultures are tested for phage quantities and higher quantity phages are selected, isolated and cultured. The isolated phage preparations then are formulated into compositions for intravenous, topical or other route of administration.

Example 5

The following example illustrates the isolation and purification of phage preparations, and then the selection of virulent phages that will be useful in effectively treating bacterial infections in mammals.

Samples are collected from individuals from sample sites such as throat swabs, blood samples, urinary samples, spinal fluid samples, nasal swabs, rectal swabs, stool samples, skin scrapings, sputum, washings from larynx and trachea, and other sources, biopsies and other sites of infectious foci. These sample sites are selected on the basis of the target bacterial microorganism such as any of the bacterial microorganisms listed above. For example, a throat swab is used to collect a sample of a strain of streptococci, a spinal fluid or blood sample is used for collecting a sample of *Neisseria meningitidis*, and a skin or abscess scraping or biopsy or swab is used for collecting a sample of *Staphylococcus aureus*.

The sample collected then is dispersed in phosphate buffered saline, pH of about 7.0, and then filtered through a membrane having a pore size ranging from 0.2 to 0.4 $\mu$m, which will retain the target bacterial organism and allow the bacteriophage to pass through. The filtrate therefore will contain bacteriophages to the target host microorganism.

Culture plates infected with the target bacterial organisms are used to screen for bacteriophages by plaque formation by standard methods.

Individual plaques then are purified and the bacteriophage viruses grown in medium containing the targeted microorganism. The mechanisms involved in the growth of bacteriophage in the presence of a host bacteria is known in the art and described in, for example, Stryer, Lubert, BIOCHEMISTRY, $3^{RD}$ ED., W. H. Freeman and Company, N.Y. (1988); Freifelder, David, MOLECULAR BIOLOGY, $2^{ND}$ ED., Jones and Bartlett, Inc., MA (1987). The growth rate is determined and documented by, for example, taking samples every two hours and titering the quantity of bacteriophage. Bacteriophage preparations achieving higher titers at earlier sampling times are selected and isolated, typically, those achieving titers higher than about $10^8$ to $10^9$ bacteriophages per plaque after about eight hours.

Upon isolation, or during growth, mutating conditions selected from mutator host, irradiation, temperature and pH extremes, ionic variation of the medium including drying or overhydration or extremes of individual ionic concentrations, and heat shock are introduced in order to maximize bacteriophage diversity (mutated bacteriophages add to the pool of bacteriophage which are to be selected) and to enhance the probability of selection of more virulent and more in vivo adaptable bacteriophages.

The selected and isolated bacteriophage samples then are subjected to an additional filtration through a filter having a pore size within the range of from about 0.2 to about 0.4 $\mu$m to isolate the bacteriophages from the culture system. To assure homogeneity of these isolated bacteriophage preparations, the steps of (i) screening the bacteriophage for plaque formation, (ii) growing bacteriophage in medium with the target microorganism, and then (iii) subjecting the bacteriophage to mutating conditions are repeated using the isolated bacteriophage preparations. The final bacteriophage preparations are titered to determine the number of plaque forming units in each preparation using methods known it the art. Freifelder, D. supra.

These purified phage preparations then are further treated and processed to remove endotoxins and other toxins using procedures known in the art such as ultrafiltration, ultracentrifugation, size exclusion chromatography and affinity chromatography. A final preparation of bacteriophage then is prepared by collating and mixing such that aliquots of the final mixture contain equal numbers of the bacteriophages.

These final preparations then are administered by injection, topical application or other means in mice, and samples from various sites such as blood and spinal fluid samples, throat swabs, nasal swabs, and the like are collected at various time intervals, for example at six hours, 24 hours, 2 days, 3 days, 4 days and 5 days. The more virulent bacteriophages are identified by plating, and these then are isolated, grown, purified and detoxified as described above.

These bacteriophage preparations then are administered to mice previously infected with the targeted bacterial microorganism, and the virulence of the bacteriophage is determined by comparing the microbial counts of treated versus non-treated animals over time. The bacteriophages with the highest anti-bacterial activity then is selected, isolated and purified. Toxin removal then can be carried out using any of the following techniques: (i) ultrafiltration through a membrane or hollow fiber with a molecular weight cut-off of $10^5$ to $10^6$ daltons; (ii) ultracentrifugation using preparations such as cesium chloride (60 to 95 g/100 ml), percoll or ficoll (50 to 80%), and sucrose or glycerol (5 to 40%) at forces of 60,000×g to 80,000×g for 2 hours (cesium chloride, sucrose and/or glycerol), or at forces of 25,000×g to 35,000×g for 20 to 30 minutes (percoll or ficoll); (iii) dialysis using the largest pore membrane that retains bacteriophages with molecular weight cut-off of $10^5$ to $10^6$ daltons; and (iv) size exclusion chromatography using preparatory columns with an exclusion pore of $10^5$ to $10^6$ daltons.

The purified and detoxified bacteriophages then are formulated into compositions suitable for administration to a mammal. A mammal suffering from a bacterial infection then can be treated by administering the bacteriophage-containing composition in an amount and for a period of time effective to treat the bacterial infection by killing the bacterial microorganisms which caused the infection.

Example 6

Purified *E. coli* bacteriophage isolates were obtained from sewage using the following procedure. About 100 $\mu$l of sewage filtrate (0.45 $\mu$m acetate filters) was mixed with about 200 $\mu$l culture of an *E. coli* isolate grown to saturation in LB medium. Tubes were incubated at room temperature for about fifteen minutes, and then 3.5 ml LB top agar (0.7% agar tempered to 50° C.) was added to the tubes, vortexed, and poured onto fresh LB plates. Plates then were incubated inverted at 37° C. overnight. Single plaques were chosen using a sterile Pasteur pipette, and the agar plug was placed in a tube containing 1 ml sterile SM buffer. One drop of chloroform was added, and the tube was vortexed briefly. The solution then was allowed to stand for at least one hour at room temperature for phage to elute from the plaque. Phage then were replated at a low density (~10 plaques per plate). A single, well isolated plaque was chosen and plated once more to produce a pure phage preparation.

To prepare high titer stock of phage preparations, about 100 $\mu$l of phage stock prepared above ($10^6$ PFU) was added to about 200 µl of an *E. coli* isolate grown to saturation. Top agar (3.5 ml LB; 0.3%) was added as described above, and poured. Plates were incubated at 37° C. overnight. If confluent lysis was achieved, 3 ml of SM buffer was added, and buffer plus overlay was scraped off using a bent glass rod and placed into a sterile 50 ml Falcon tube. Several drops of chloroform were added and the tubes were shaken gently for about ten minutes. Samples then were spun at about 2800 rpm for twenty minutes, the supernatant was removed and filtered (0.45 µm acetate filters). Serial dilutions then were prepared to determine the phage titer. The phage preparations were stored in SM buffer with a drop of chloroform at 4° C.

These bacteriophage preparations then were tested against *E. coli* isolates using a ratio of about 1:100 (phage:bacteria) by infecting about 5 ml aliquot of *E. coli* with the appropriate amount of phage, and the tubes-were allowed to remain at room temperature for fifteen minutes. About 1 liter of LB was inoculated, and incubated overnight at 37° C. with vigorous shaking (250 rpm). In the morning, 10 ml chloroform/l was added and shaking continued for fifteen minutes. Bacterial debris was pelleted by centrifugation at 10,000 rpm for fifteen minutes at 4° C. (Sorvall GSA rotor). Supernatant was poured off into a clean flask, and the volume was measured. Then, about 5M NaCl (1 ml/l 100 ml) was added and mixed by gentle stirring. PEG 8000 (10 g/100 ml) then was added and allowed to dissolve completely. Phage precipitated overnight at 4° C. In the morning, the flask was swirled to resuspend the precipitate, and centrifuged at 5000 rpm for twenty minutes at 4° C. The supernatant was decanted, and tubes inverted on a paper towel to dry for several minutes. Pellets then were resuspended by gentle swirling in a total volume of 5 ml TM buffer.

CsCl was added to a density of 1.5 g/ml, and the solution was placed in ultracentrifuge tubes. Tubes were filled to the neck with premade CsCl solution (d=1.5 g/ml). Samples were centrifuged at 34 K overnight at 15° C. (Sorval 865.1 Ti rotor). After centrifugation, each band was carefully drawn off using an 18 gauge needle, and placed in a new tube. Each sample was dialyzed (Spectra-Por Membrane, Molecular Weight Cut-Off 50,000) in 1.5 L low salt buffer with gentle stirring for about one hour. This step was repeated twice more, and a titer of about $10^{11}$ was obtained for each phage. The phage preparations then were stored in low salt buffer at 4° C.

Figure 1:
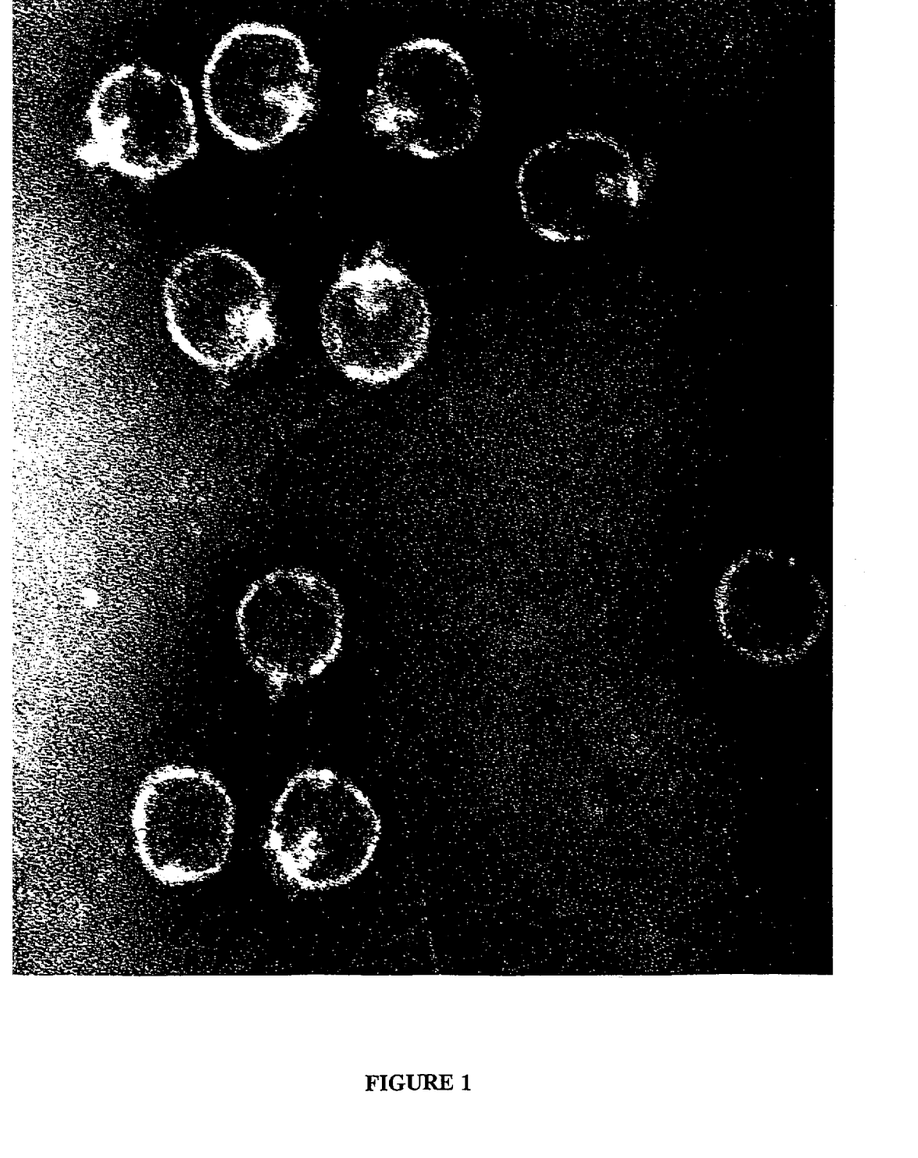
FIG. 1 represents an electron micrograph (magnified×450,000), of 173A *E. coli* bacteriophage, negatively stained, from Example 6.
Figure 2:
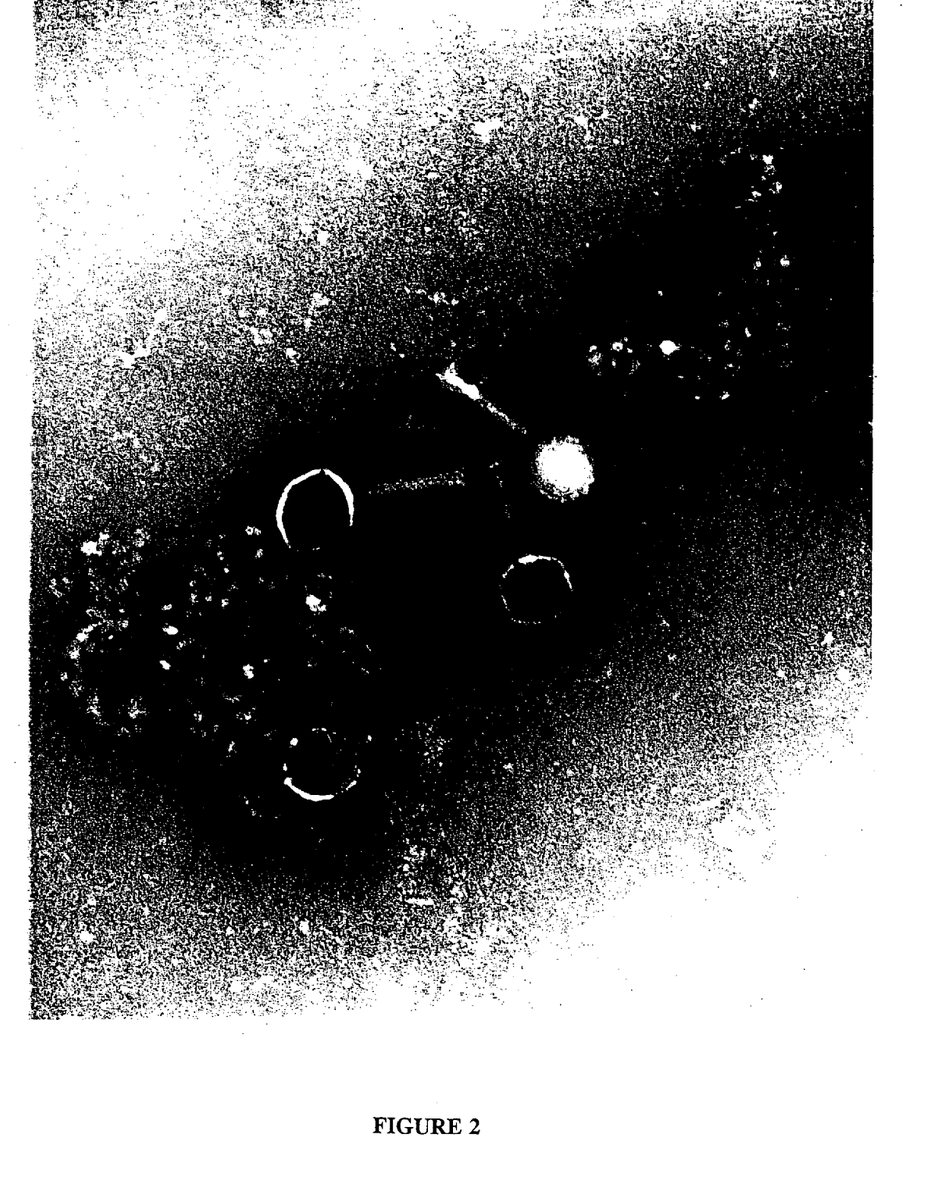
FIG. 2 represents an electron micrograph (magnified×225,000) of 146A *E. coli* bacteriophage, negatively stained, from Example 6.
Figure 3:
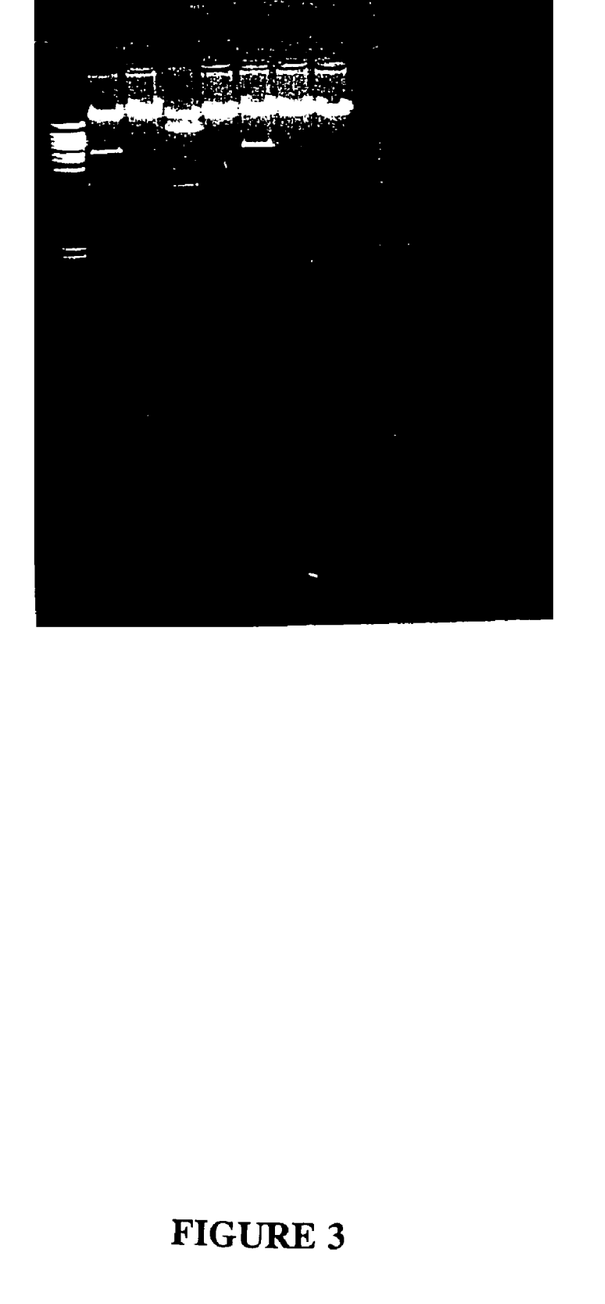
FIG. 3 represents DNA fingerprinting of 173A *E. coli* bacteriophage of Example 6.
Figure 4:
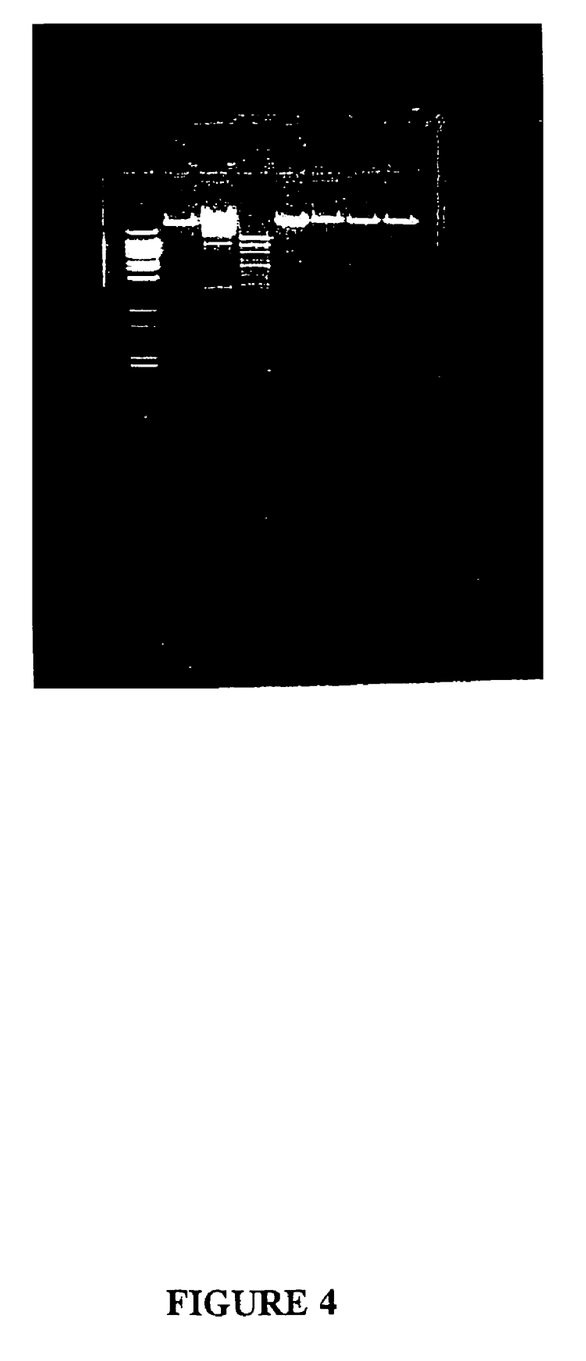
FIG. 4 represents DNA fingerprinting of 146A *E. coli* bacteriophage of Example 6.

Two particularly virulent preparations were selected on the basis of concentration and isolate sensitivity. CsCl purified preparations 146A and 173A were capable of killing the majority of different isolates, and were virulent at a concentration of 100 times less than the least virulent preparation. Purified 146A and 173A phage preparations were tested against 52 different *E. coli* isolates, whereby 146A plaqued against 22 isolates (42%) and 173A plaqued against 20 isolates (38%). Combined, these two phage preparations were effective against 31 of the 52 isolates (60%). In comparison, a purified 222A phage preparation was found to be effective in killing only 6 isolates (11.5%). Purified 146A and 173A *E. coli* bacteriophage preparations were then characterized by: (i) plaque morphology (the 14.6A preparations provided clear plaques of 1–2 mm with defined edges, and the 173A preparations provided plaques of 4–6 mm with clear centers of 2–3 mm and turbid haloes); (ii) electron microscopy (FIGS. 1 and 2); and (iii) DNA fingerprinting analysis (FIGS. 3 and 4). Samples of virulent bacteriophage 146A and 173A preparations were deposited in the ATCC, 12301 Parklawn Drive, Rockville, Md., 20852, on Apr. 15, 1997 and accorded ATCC accession Nos. 55950 and 55951, respectively.

Example 7

Figure 5:
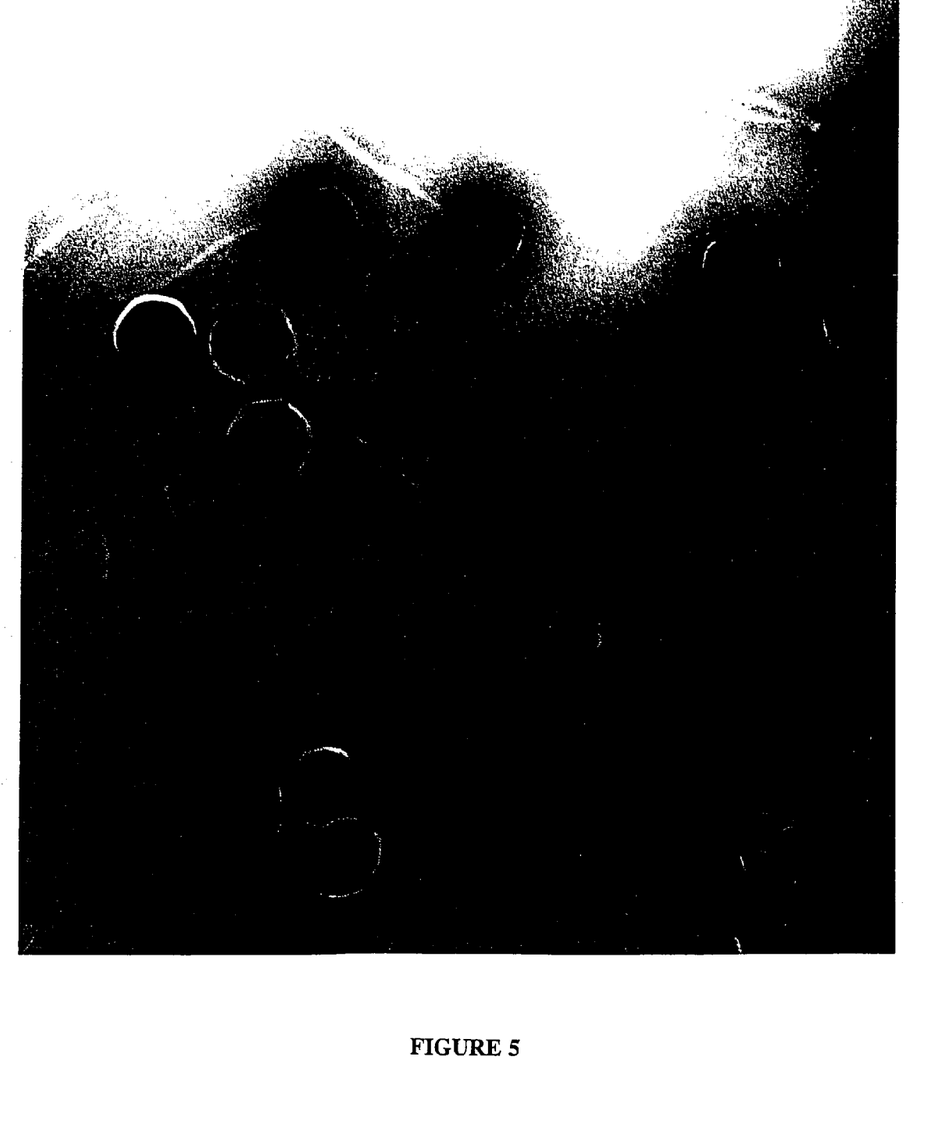
FIG. 5 represents an electron-micrograph (magnified×225,000) of 262A *C. fruendii* bacteriophage, negatively stained, from Example 7.
Figure 6:
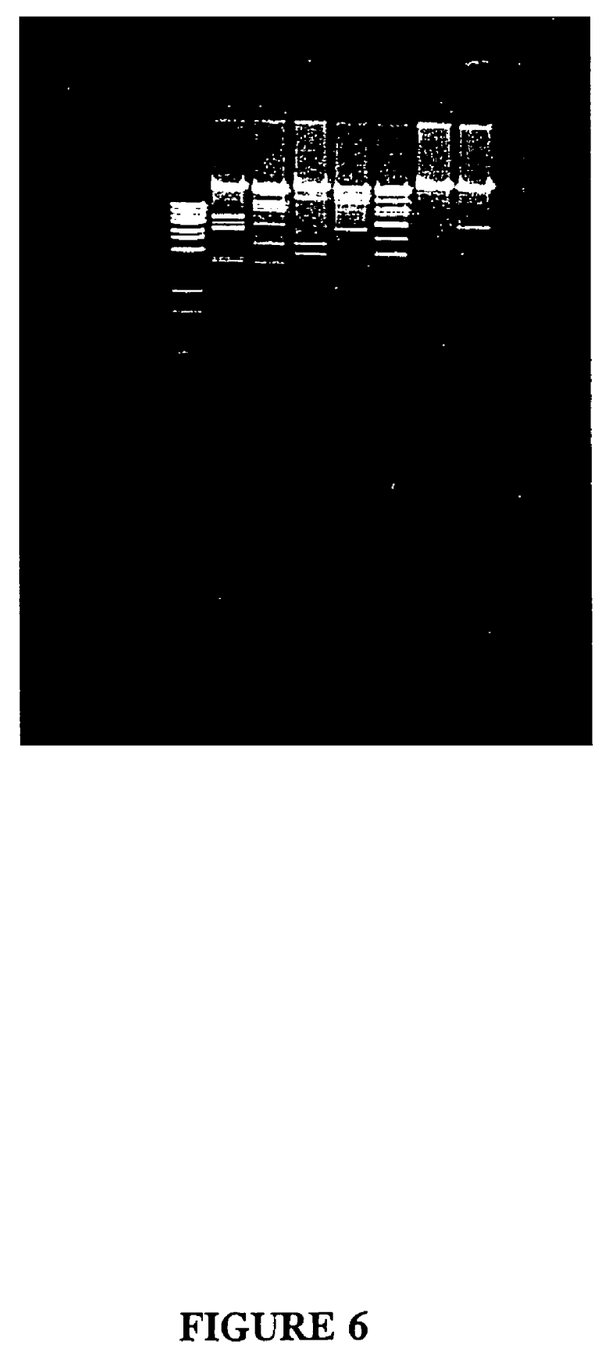
FIG. 6 represents DNA fingerprinting of 174A *K. oxytoca* bacteriophage of Example 7.

Bacterial cultures of *Citrobacter fruendii* and from *Klebsiella oxytoca* were obtained from urinary samples and purified. Host-specific plaque purified nontoxic bacteriophage preparations were selected, isolated, and purified from sewage filtrate using the procedures outlined above in Example 6, except that purified urinary cultures of *Citrobacter fruendii* and *Klebsiella oxytoca* were used. Virulent bacteriophage 262A preparations against *C. fruendii* were characterized by: (i) plaque morphology (the *C. fruendii* plaques had diameters of 2–4 mm with irregular edges and distinct centers; (ii) electron microscopy (FIG. 5); and (iii) DNA fingerprinting analysis. A samples of virulent bacteriophage 262A preparation was deposited in the ATCC at the above address, on Apr. 15, 1997 and accorded ATCC accession No. 55955. Virulent bacteriophage 174 preparations against *K. oxytoca* were characterized similarly by plaque morphology, electron microscopy and DNA fingerprint analysis (FIG. 6). A sample of virulent bacteriophage 174A preparation was deposited in the ATCC at the above address on Apr. 15, 1997 and accorded ATCC accession No. 55956.

Example 8

A number of purified clinical samples of *Streptococcus pyogenes* were obtained, some from pus samples, and most from throat samples. Three phage preparations were obtained from ATCC: 12202-B1, 12203-B1 and 12204-B1. An additional clinical strep phage was obtained, A25, which appears to be to be identical to ATCC phage 12204-B1. After preparing A25 in accordance with the present invention, however, the resulting phage preparation was non-toxic, highly purified, host-specific, virulent and had a wide host range whereas the commercially available phage 12204-B1 did not have all of these characteristics. Bacteriophage preparations were tested against *S. pyogenes* isolates as described in Example 6 above, and the bacteriophage A25 preparation was found to be especially virulent on the basis of concentration and isolate sensitivity. The bacteriophage A25 preparations were characterized by plaque morphology (tiny plaques and circles of complete lysis) and electron microscopy.

Example 9

A number of clinical samples of *Staphylococcus aureus* were obtained, and purified as described above in example 7. These samples were isolated from pus samples, throat samples, and nose swabs. Three phage preparations were obtained from ATCC: ATCC27706-B1 (equivalent to CDC phage 83A); ATCC27708-B1; and ATCC 15752-B1 (from nontypeable *S. aureus*). In addition, two clinical phage preparations were obtained, 11 φ and 80α.

Figure 7:
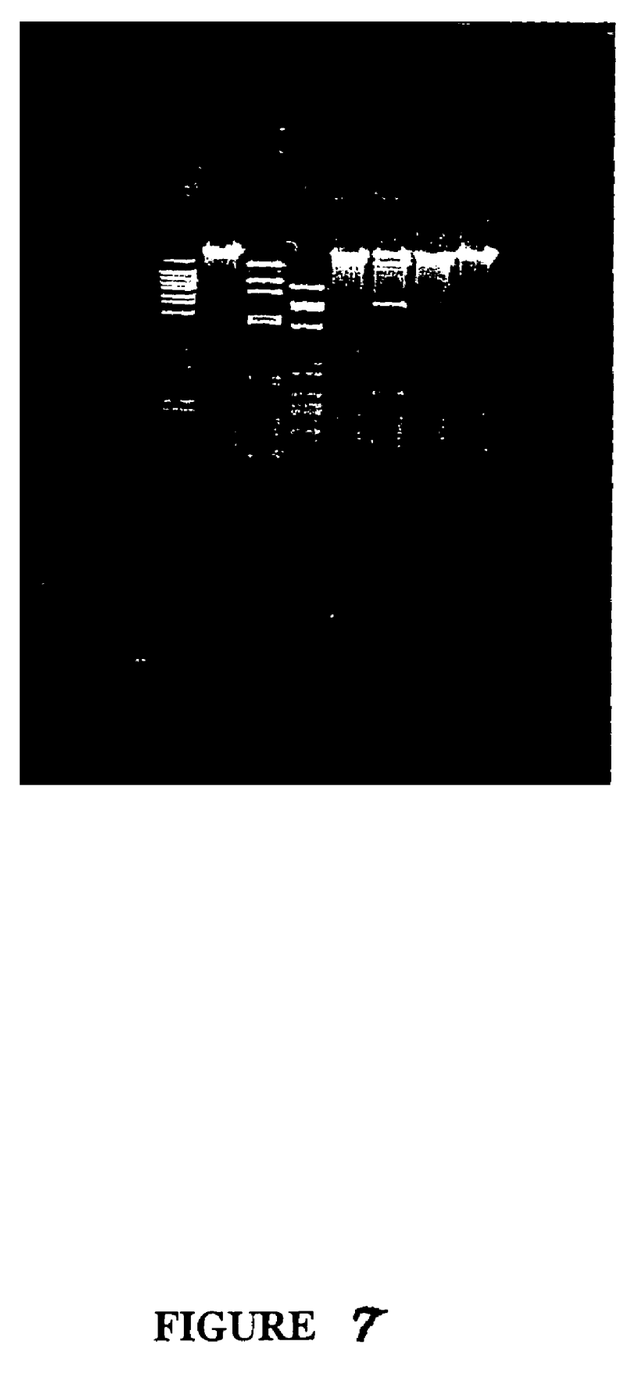
FIG. 7 represents DNA fingerprinting of 83A *S. aureus* bacteriophage of Example 9.

Bacteriophage preparations were tested against *S. aureus* isolates as described in Example 6 above, and the bacteriophage 83A was found to be particularly virulent. Out of nine different host samples of *S. aureus*, bacteriophage 83A was effective in killing 5 (56%), whereas the next most virulent bacteriophage after undergoing the above treatment, was effective in killing only 1 (11%). Thus, 83A bacteriophage had a wider host range than and killed 400% more bacteria. Bacteriophage obtained directly from the ATCC, and the clinical samples that did not undergo the above treatment (i.e., wild-type bacteriophage), were not effective (0%). The bacteriophage 83A preparations were characterized by plaque morphology (clear plaques of 1–2 mm with defined edges, electron microscopy, and DNA fingerprint analysis (FIG. 9).

While the invention has been described with reference to particularly preferred embodiments and examples, those skilled in the art will appreciate that various modifications can be made to the invention without significantly departing from the spirit and scope thereof. All of the above-mentioned documents are incorporated by reference herein in their entirety.

What is claimed is:

1. A method of treating a mammal suffering from bacterial infection comprising administering to the mammal an effective amount of a composition comprising:
   (a) a purified, host-specific, non-toxic, wide host-range, and virulent bacteriophage preparation, wherein:
      (1) the bacteriophage preparation consists essentially of two or more bacteriophage strains, wherein each bacteriophage strain is specific for the bacterial infection treated and is selected against one of the group consisting of staphylococci, hemophilii, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex;*
      (2) at least two of the bacteriophage strains are isolated against different strains of bacterial organisms; and
      (3) each bacteriophage strain is effective in killing, in vitro, bacteria from at least about 50% of bacterial isolates, wherein the isolates are from the same strain of bacterial organism as that from which the bacteriophage strain is isolated; and
      (4) the bacteriophage preparation can be safely administered to patients or mammals in need; and
   (b) a pharmaceutically acceptable carrier, wherein the carrier is in the form of a liposome.

2. A method of treating a mammal suffering from bacterial infection comprising administering to the mammal an effective amount of a composition comprising:
   (a) a purified, host-specific, non-toxic, wide host-range, and virulent bacteriophage preparation, wherein:
      (1) the bacteriophage preparation consists essentially of two or more bacteriophage strains, wherein each bacteriophage strain is specific for the bacterial infection treated and is selected against one of the group consisting of staphylococci, hemophilia, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex;*
      (2) at least two of the bacteriophage strains are isolated against different strains of bacterial organisms; and
      (3) each bacteriophage strain is effective in killing, in vitro, bacteria from at least about 50% of bacterial isolates, wherein the isolates are from the same strain of bacterial organism as that from which the bacteriophage strain is isolated; and
      (4) the bacteriophage preparation can be safely administered to patients or mammals in need; and
   (b) a pharmaceutically acceptable carrier, wherein the carrier is a dendrimer.

3. A method of treating a mammal suffering from bacterial infection, comprising administering to the mammal an effective amount of a composition comprising:
   (a) a purified, host-specific, non-toxic, wide host-range, and virulent bacteriophage preparation, wherein the bacteriophage preparation consists essentially of two or more bacteriophage strains, wherein each bacteriophage strain is selected against one of the group consisting of staphylococci, hemophilia, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex*, and each bacteriophage strain is effective in killing bacteria from at least 50% of bacterial isolates; and
   (b) a pharmaceutically acceptable carrier, wherein the carrier is in the form of a liposome.

4. A method of treating a mammal suffering from bacterial infection, comprising administering to the mammal an effective amount of a composition comprising:
   (a) a purified, host-specific, non-toxic, wide host-range, and virulent bacteriophage preparation, wherein the bacteriophage preparation consists essentially of two or more bacteriophage strains, wherein each bacteriophage strain is selected against one of the group consisting of staphylococci, hemophilia, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex*, and each bacteriophage strain is effective in killing bacteria from at least 50% of bacterial isolates; and
   (b) a pharmaceutically acceptable carrier, wherein the carrier is a dendrimer.

5. A method of treating a mammal suffering from bacterial infection comprising administering to the mammal an effective amount of a composition comprising:
   (a) a purified, host-specific, non-toxic, wide host-range, and virulent bacteriophage preparation, wherein:
      (1) the bacteriophage preparation consists essentially of two or more bacteriophage strains, wherein each bacteriophage strain is specific for the bacterial infection treated and is selected against one of the group consisting of staphylococci, hemophilia, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex;*
      (2) at least two of the bacteriophage strains are isolated against different strains of bacterial organisms; and
      (3) each bacteriophage strain is effective in killing, in vitro, bacteria from at least about 50% of bacterial isolates, wherein the isolates are from the same strain of bacterial organism as that from which the bacteriophage strain is isolated; and
      (4) the bacteriophage preparation can be safely administered to patients or mammals in need; and
      (5) the bacteriophage preparation is the isolated bacteriophage composition designated 146A and deposited at the American Type Culture Collection (ATCC) under Accession No. 55950 on Apr. 15, 1997; and
   (b) a pharmaceutically acceptable carrier.

6. A method of treating a mammal suffering from bacterial infection comprising administering to the mammal an effective amount of a composition comprising:
(a) a purified, host-specific, non-toxic, wide host-range, and virulent bacteriophage preparation, wherein:
(1) the bacteriophage preparation consists essentially of two or more bacteriophage strains, wherein each bacteriophage strain is specific for the bacterial infection treated and is selected against one of the group consisting of staphylococci, hemophilii, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptosoirex;*
(2) at least two of the bacteriophage strains are isolated against different strains of bacterial organisms; and
(3) each bacteriophage strain is effective in killing, in vitro, bacteria from at least about 50% of bacterial isolates, wherein the isolates are from the same strain of bacterial organism as that from which the bacteriophage strain is isolated; and
(4) the bacteriophage preparation can be safely administered to patients or mammals in need; and
(5) the bacteriophage preparation is the isolated bacteriophage composition designated 173A and deposited at the American Type Culture Collection (ATCC) under Accession No. 55955 on Apr. 15, 1997; and
(b) a pharmaceutically acceptable carrier.

7. A method of treating a mammal suffering from bacterial infection comprising administering to the mammal an effective amount of a composition comprising:
(a) a purified, host-specific, non-toxic, wide host-range, and virulent bacteriophage preparation, wherein:
(1) the bacteriophage preparation consists essentially of two or more bacteriophage strains, wherein each bacteriophage strain is specific for the bacterial infection treated and is selected against one of the group consisting of staphylococci, hemophilii, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex;*
(2) at least two of the bacteriophage strains are isolated against different strains of bacterial organisms; and
(3) each bacteriophage strain is effective in killing, in vitro, bacteria from at least about 50% of bacterial isolates, wherein the isolates are from the same strain of bacterial organism as that from which the bacteriophage strain is isolated; and
(4) the bacteriophage preparation can be safely administered to patients or mammals in need; and
(5) the bacteriophage preparation is the isolated bacteriophage composition designated 262A and deposited at the American Type Culture Collection (ATCC) under Accession No. 55951 on Apr. 15, 1997; and
(b) a pharmaceutically acceptable carrier.

8. A method of treating a mammal suffering from bacterial infection comprising administering to the mammal an effective amount of a composition comprising:
(a) a purified, host-specific, non-toxic, wide host-range, and virulent bacteriophage preparation, wherein:
(1) the bacteriophage preparation consists essentially of two or more bacteriophage strains, wherein each bacteriophage strain is specific for the bacterial infection treated and is selected against one of the group consisting of staphylococci, hemophilia *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex;*
(2) at least two of the bacteriophage strains are isolated against different strains of bacterial organisms; and
(3) each bacteriophage strain is effective in killing, in vitro, bacteria from at least about 50% of bacterial isolates, wherein the isolates are from the same strain of bacterial organism as that from which the bacteriophage strain is isolated; and
(4) the bacteriophage preparation can be safely administered to patients or mammals in need; and
(5) the bacteriophage preparation is the isolated bacteriophage composition designated 174A and deposited at the American Type Culture Collection (ATCC) under Accession No. 55956 on Apr. 15, 1997; and
(b) a pharmaceutically acceptable carrier.

9. A method of treating a mammal suffering from bacterial infection, comprising administering to the mammal an effective amount of a composition comprising:
(a) a purified, host-specific, non-toxic, wide host-range, and virulent bacteriophage preparation, wherein the bacteriophage preparation consists essentially of two or more bacteriophage strains, wherein each bacteriophage strain is selected against one of the group consisting of staphylococci, hemophilia, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex*, and each bacteriophage strain is effective in killing bacteria from at least 50% of bacterial isolates and wherein the bacteriophage preparation is the isolated bacteriophage composition designated 146A and deposited at the American Type Culture Collection (ATCC) under Accession No. 55950 on Apr. 15, 1997; and
(b) a pharmaceutically acceptable carrier.

10. A method of treating a mammal suffering from bacterial infection, comprising administering to the mammal an effective amount of a composition comprising:
(a) a purified, host-specific, non-toxic, wide host-range, and virulent bacteriophage preparation, wherein the bacteriophage preparation consists essentially of two or more bacteriophage strains, wherein each bacteriophage strain is selected against one of the group consisting of staphylococci, hemophilii, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex*, and each bacteriophage strain is effective in killing bacteria from at least 50% of bacterial isolates and wherein the bacteriophage preparation is the isolated bacteriophage composition designated 173A and deposited at the American Type Culture Collection (ATCC) under Accession No. 55955 on Apr. 15, 1997; and
(b) a pharmaceutically acceptable carrier.

11. A method of treating a mammal suffering from bacterial infection, comprising administering to the mammal an effective amount of a composition comprising:

(a) a purified, host-specific, non-toxic, wide host-range, and virulent bacteriophage preparation, wherein the bacteriophage preparation consists essentially of two or more bacteriophage strains, wherein each bacteriophage strain is selected against one of the group consisting of staphylococci, hemophilii, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex*, and each bacteriophage strain is effective in killing bacteria from at least 50% of bacterial isolates and wherein the bacteriophage preparation is the isolated bacteriophage composition designated 262A and deposited at the American Type Culture Collection (ATCC) under Accession No. 55951 on Apr. 15, 1997; and (b) a pharmaceutically acceptable carrier.

12. A method of treating a mammal suffering from bacterial infection, comprising administering to the mammal an effective amount of a composition comprising:

(a) a purified, host-specific, non-toxic, wide host-range, and virulent bacteriophage preparation, wherein the bacteriophage preparation consists essentially of two or more bacteriophage strains, wherein each bacteriophage strain is selected against one of the group consisting of staphylococci, hemophilia, *helicobacter, mycobacterium*, mycoplasmi, streptococci, neisserii, *klebsiella, enterobacter, proteus, bacteriodes, pseudomonas, borrelii, citrobacter, escherichia, salmonella, propionibacterium, treponema, shigella*, enterococci, and *leptospirex*, and each bacteriophage strain is effective in killing bacteria from at least 50% of bacterial isolates and wherein the bacteriophage preparation is the isolated bacteriophage composition designated 174A and deposited at the American Type Culture Collection (ATCC) under Accession No. 55956 on Apr. 15, 1997; and (b) a pharmaceutically acceptable carrier.

\* \* \* \* \*